(12) United States Patent
Kliem

(10) Patent No.: US 12,420,121 B2
(45) Date of Patent: Sep. 23, 2025

(54) OXYGEN MASK FOR SUPPLYING OXYGEN TO A PERSON

(71) Applicant: Airbus Operations GmbH, Hamburg (DE)

(72) Inventor: Patricia Kliem, Hamburg (DE)

(73) Assignee: Airbus Operations GmbH, Hamburg (DE)

( * ) Notice: Subject to any disclaimer, the term of this patent is extended or adjusted under 35 U.S.C. 154(b) by 652 days.

(21) Appl. No.: 17/610,322

(22) PCT Filed: Aug. 25, 2020

(86) PCT No.: PCT/EP2020/073710
§ 371 (c)(1),
(2) Date: Nov. 10, 2021

(87) PCT Pub. No.: WO2021/037830
PCT Pub. Date: Mar. 4, 2021

(65) Prior Publication Data
US 2022/0241621 A1 Aug. 4, 2022

(30) Foreign Application Priority Data
Aug. 30, 2019 (DE) .......................... 102019123331.3

(51) Int. Cl.
| | | |
|---|---|---|
| *A62B 18/08* | (2006.01) | |
| *A62B 7/12* | (2006.01) | |
| *A62B 7/14* | (2006.01) | |
| *A62B 18/02* | (2006.01) | |

(Continued)

(52) U.S. Cl.
CPC .............. *A62B 18/084* (2013.01); *A62B 7/12* (2013.01); *A62B 7/14* (2013.01); *A62B 18/025* (2013.01);

(Continued)

(58) Field of Classification Search
CPC ............ B64D 2231/025; A62B 18/025; A62B 18/084; A62B 7/14; A62B 23/025;

(Continued)

(56) References Cited

U.S. PATENT DOCUMENTS 2,378,929 A * 6/1945 Joyce .................. A41D 13/1146
55/505
D344,608 S * 2/1994 Goryachy .................... D24/164

(Continued)

FOREIGN PATENT DOCUMENTS

GB 697762 A * 3/1951
KR 200314045 Y1 * 5/2003

(Continued)

OTHER PUBLICATIONS

KR 200314045 machine translation (Year: 2003).*

(Continued)

*Primary Examiner* — Victoria Murphy
*Assistant Examiner* — Sara K Toich
(74) *Attorney, Agent, or Firm* — Lerner David LLP

(57) ABSTRACT

The invention relates to an oxygen mask for supplying oxygen to a person, which can be modified for use on differently sized faces. The oxygen mask has a holding frame, which has a first cross-brace and a second cross-brace, a substantially gas-impermeable material arranged on the holding frame and which can be stretched between the first cross-brace and the second cross-brace, a headband connected to the holding frame, an exhalation valve arranged on the material and penetrating the material, and an oxygen supply line for providing oxygen to an inside of the oxygen mask, wherein the first cross-brace and the second cross-brace are arranged in two lateral holders, which are opposite each other, wherein at least the first cross-brace is flexible and wherein the distance of the lateral holders to (Continued)

each other is adjustable at least between a first and a second distance.

14 Claims, 3 Drawing Sheets

(51) Int. Cl.
    *A62B 18/10*     (2006.01)
    *B64D 25/00*     (2006.01)
(52) U.S. Cl.
    CPC .............. *A62B 18/10* (2013.01); *B64D 25/00* (2013.01); *B64D 2231/025* (2013.01)
(58) Field of Classification Search
    CPC ........ A62B 9/04; A62B 25/005; A61M 16/06; A61M 16/0605; A41D 13/1146
    See application file for complete search history.

(56) References Cited

U.S. PATENT DOCUMENTS

| | | | | |
|---|---|---|---|---|
| 2004/0182396 | A1* | 9/2004 | Dennis | ................... A62B 18/02 128/205.25 |
| 2005/0150495 | A1* | 7/2005 | Rittner | ................ A62B 18/025 128/205.13 |
| 2006/0219246 | A1 | 10/2006 | Dennis | |
| 2009/0078262 | A1* | 3/2009 | Gebrewold | .......... A62B 23/025 29/428 |
| 2014/0345621 | A1* | 11/2014 | Zack | ...................... A61M 16/06 29/428 |
| 2018/0243592 | A1* | 8/2018 | Gordon | ................ A62B 18/084 |

FOREIGN PATENT DOCUMENTS

| | | | |
|---|---|---|---|
| KR | 20060083536 A | * | 7/2006 |
| KR | 20100010454 U | * | 10/2010 |
| WO | 2009038934 A1 | | 3/2009 |

OTHER PUBLICATIONS

KR 20060083536 machine translation (Year: 2006).*
KR 20100010454 machine translation (Year: 2010).*
International Search Report for Application No. PCT/EP2020/073710, dated Nov. 19, 2020, 3 pages.

* cited by examiner

I

II

III

OXYGEN MASK FOR SUPPLYING OXYGEN TO A PERSON

CROSS-REFERENCE TO RELATED APPLICATIONS

The present application is a national phase entry under 35 U.S.C. § 371 of International Application No. PCT/EP2020/073710 filed Aug. 25, 2020, published in German, which claims priority from German Application No. 102019123331.3 filed Aug. 30, 2019.

TECHNICAL FIELD

The invention relates to an oxygen mask for supplying oxygen to a person, a system for providing oxygen to oxygen masks in an aircraft, and an aircraft with a passenger cabin and at least one such system.

BACKGROUND OF THE INVENTION

Oxygen masks in passenger aircraft are usually designed for use by adults. In a system for providing oxygen at a continuous flow of oxygen, an oxygen-enriched environment is created within the oxygen mask on an inside directed toward the person. Even if the air is able to escape from the oxygen mask because of leaks, the user still receives a sufficient amount of oxygen.

In more modern oxygen systems, however, it could become necessary to use oxygen masks that are largely free of leakage, so that a person can be supplied with an oxygen flow that is sufficient in accordance with EASA approval guidelines CS25. This means that the oxygen mask must fit tight on the face of the person concerned. Adapted oxygen masks may therefore be particularly useful for babies and infants and for people with beards.

SUMMARY OF THE INVENTION

It is therefore an object of the invention to propose an oxygen mask that can be adapted to different face sizes and beards without modifications, without an additional mask having to be procured if necessary.

The object is achieved by an oxygen mask having the features of independent claim 1. Advantageous embodiments and developments can be found in the subclaims and in the following description.

An oxygen mask for supplying oxygen to a person is proposed, having a holding frame which has at least one transverse web, a substantially gas-impermeable fabric which is arranged on the holding frame and is stretchable by the at least one transverse web, a headband connected to the holding frame, an exhalation valve arranged on the fabric and passing through the fabric, and an oxygen supply line for providing oxygen to an inside of the oxygen mask, wherein the at least one transverse web is arranged in two lateral holders lying opposite each other, wherein the at least one transverse web is flexible, and wherein the distance of the lateral holders from each other is adjustable at least between a first and a second distance.

The oxygen mask according to the invention is therefore composed of two main components, which are supplemented by an exhalation valve and an oxygen supply line. A core principle lies in a fabric being stretched with the aid of a holding frame, which has at least one transverse web. A transverse web is a component that runs in a transverse direction of the oxygen mask. This means that a transverse web extends from one side of the oxygen mask to an opposite side. A transverse web can be used which extends approximately over a nose region. Another transverse web could be located in a chin region. If a plurality of transverse webs are used, these could be similar to one another or be designed differently and thus have different cross sections, different lengths or different materials. One transverse web could have a considerably smaller cross section, for example, and be very elastic, similar to a rubber band.

The at least one transverse web is designed to stretch and hold the fabric. The stretching does not mean that the fabric is stretched taut between a plurality of transverse webs. Instead, the fabric could also have a curved shape following the person's face, and the at least one transverse web helps maintain this shape.

By virtue of the flexibility of the at least one transverse web, the oxygen mask is able, in particular, to nestle on the nose and mouth region. It is preferable here that, when using a plurality of transverse webs, all of the transverse webs of the oxygen mask are flexible. The oxygen mask can then be put on by a user and assume a pronounced curvature or arc shape in all spatial directions.

The headband, which is connected to the holding frame, allows the oxygen mask to be fixed to the user's head. The headband is preferably arranged on the lateral holders, such that the latter are fixed in an outer position and the headband does not influence the course of the at least one transverse web. The lateral holders can accordingly form a mechanical interface between the headband and the fabric.

The exhalation valve allows used air to be discharged in a targeted manner through an overpressure that occurs in the oxygen mask during exhalation. It is in particular at a distance from one end of the oxygen supply line, such that no undesired loss of oxygen occurs.

To adapt the oxygen mask to the size of the user's face, the lateral holders are able to adopt a variable distance from one another. This means that the width of the oxygen mask can be increased if necessary. It is particularly recommended for the oxygen mask to be stowed with the smallest possible width, such that it can be taken hold of by the user, for example in order to widen the oxygen mask by an easy and intuitive hand movement. It is conceivable to do this by pulling the lateral holders apart. By virtue of the flexible at least one transverse web, the area spanned by the fabric can likewise be enlarged, if necessary. For this purpose, when using a plurality of transverse webs, the latter are preferably spaced apart from one another in a transverse direction.

With the oxygen mask according to the invention, different characteristics of the user can be taken into account, and the oxygen mask is able to lie flush and sealingly on the user's face. Babies and also infants can be optimally supplied with oxygen from an oxygen mask. Even people with beards can put the oxygen mask on in such a way that the whole beard is spanned by the fabric and the at least one transverse web is able to lie flush on adjacent regions of skin. No improvised solutions are necessary, and practically all conceivable users can use the oxygen mask according to the invention. Each seat can therefore be equipped with this oxygen mask, and no special oxygen masks have to be carried separately.

In an advantageous embodiment, the at least one transverse web is mounted displaceably on or in the lateral holders. The displaceability here is in particular along the longitudinal extent of the relevant transverse web. It is therefore easily possible for the user to increase the width of the oxygen mask by pulling the lateral holders outward to the sides. The displaceable mounting should be mechanically as simple as possible, such that a reliable function can be guaranteed and the lowest possible additional weight results from this displaceability.

Preferably, at least one of the lateral holders for the at least one transverse web has a rectilinear cavity which is adapted to the relevant transverse web, such that the relevant transverse web is insertable into the cavity to different depths. The lateral holder is therefore able to receive the transverse web very easily in mechanical terms and enclose it circumferentially. By pulling the lateral holder in the direction of the end of the transverse web, the latter can therefore slide along the cavity and thus increase its effective length. It is particularly preferable that the transverse web and/or the cavity is provided with a surface having a high coefficient of friction and/or that such a tight fit is selected that displacement is possible only by overcoming a certain resistance and, consequently, the transverse web remains in a position to which it has been displaced.

In an advantageous embodiment, the cavity and the relevant transverse web could have a limiting device which is designed to prevent the transverse web from being pulled out completely. In particular, if a considerable tensile force is provided for the pulling out in order to increase the width, the transverse web should be prevented from accidentally sliding completely out from the cavity. The limiting device can be used to provide a type of mechanical abutment, which also provides haptic feedback that the maximum width has been reached.

The limiting device is particularly preferably in the form of an end-side thickening of the relevant transverse web and an end-side tapering of the cavity. In an end position, the end-side thickening comes into surface contact with the tapering of the cavity, such that further displacement is prevented.

The fabric is preferably stretchable between a first transverse web and a second transverse web. The first transverse web could be provided for the nose region for example, and the second transverse web for the chin region of the person. Both transverse webs could have the same or a similar cross section and a similar or the same material. In particular, it would also be conceivable for one of the first transverse web and second transverse web to be designed as a type of rubber band or another elastic element. This could be firmly connected to the lateral holders or to a fabric edge.

The oxygen mask could have a third transverse web, which is arranged between the first transverse web and the second transverse web. The third transverse web is therefore arranged in the transverse direction between the first and the second transverse web. It could give the oxygen mask greater stability.

The lateral holders could furthermore be formed from an elastic material. The elastic material also gives the lateral holders a certain shapeability in order to adapt the oxygen mask ideally to the respective user. It is conceivable that the lateral holders are produced from the same material as the transverse webs.

It is preferable that the at least one transverse web has a preformed curvature in parts, which is shaped to nestle on the person's nose. The preformed curvature can be used not only to improve the adaptation of the shape of the oxygen mask, but it could also intuitively show a person how to put on the oxygen mask.

Furthermore, it may also be advisable for the at least one transverse web to be slightly curved overall, such that an intended inside directed toward the person, and in particular of concave shape, is adopted and immediately recognized.

In an advantageous embodiment, the lateral holders have a plurality of holding portions for receiving a respective transverse web, wherein the holding portions are arranged on a hinge, which is designed to fan the holding portions out variably in relation to one another for adaptation to the person. The holding portions can be fanned out in a desired manner for adaptation to the user, such that the fabric spans a surface area of greater or lesser size. The hinge can be of a very simple design and can be limited to a securing element that penetrates the individual holding portions at a common point. The securing element could, for example, be a rod-shaped element that is produced in particular from the same material as the lateral holders.

It is preferred if the lateral holders and the at least one transverse web are made from silicone, a silicone-like material, an elastomer or a rubber-like material. In this way, the at least one transverse web is very flexible and elastic and adapts directly to the shape of the user's head when it is placed on the latter.

To adjust the headband, it may be expedient if the headband has two stiff end portions, each of which is inserted into a toothed recess, wherein the headband and the toothed recesses are designed to change an effective length of the headband in increments. A toothing would be able in particular to interact with grooves on the stiff end portions such that, by means of a tensile force on the headband, individual grooves can be skipped over by the toothing, and there is always at least a slight locking action in at least one groove. Since the end portions are stiff, it is also conceivable, in addition to a pulling movement, for the end portions to be pressed into the associated recesses. The effective length of the headband could thus be both increased and decreased.

The oxygen supply line could furthermore protrude through the fabric to the inside of the oxygen mask. The opening of the oxygen supply line could end flush with the fabric on the inside.

The invention further relates to a system for providing oxygen to oxygen masks in an aircraft. The system has an oxygen source and one or more oxygen masks according to one of the preceding claims, wherein the oxygen supply line of the oxygen masks are each connectable to the oxygen source.

The invention also relates to an aircraft having a passenger cabin and at least one system as described above.

BRIEF DESCRIPTION OF THE FIGURES

Further features, advantages and possible uses of the present invention will emerge from the following description of the exemplary embodiments and from the figures. Here, all of the features described and/or illustrated in the figures form the subject matter of the invention individually and in any desired combination, even independently of the combination of said features in the individual claims or the back-references thereof. Furthermore, in the figures, the same reference signs are used for identical or similar objects.

DETAILED ILLUSTRATION OF EXEMPLARY EMBODIMENTS

Figure 1:
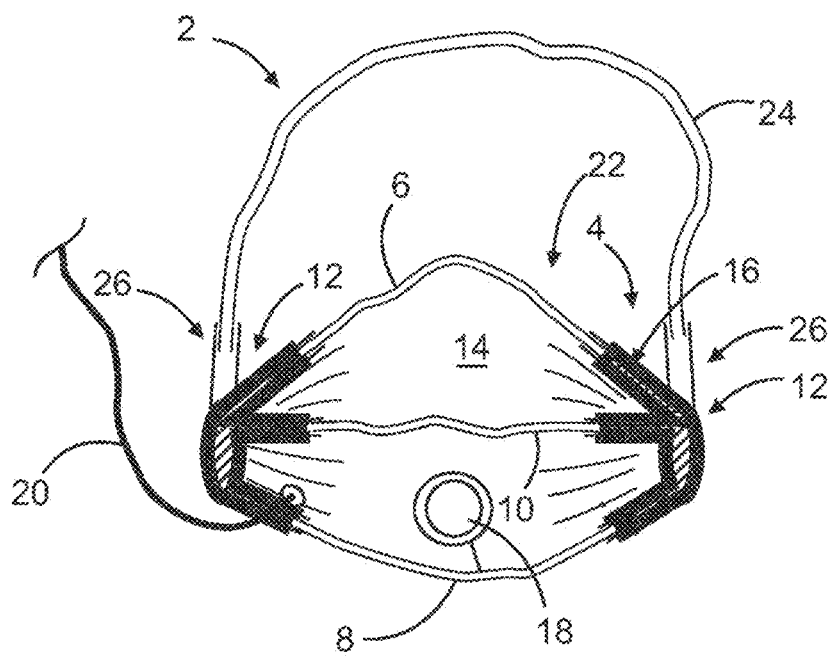
FIG. 1 shows an oxygen mask in a front view.

FIG. 1 shows an oxygen mask 2 for supplying oxygen to a person. The oxygen mask 2 can be provided in particular in a cabin of a means of transport, for example of an aircraft. The oxygen mask 2 has a holding frame 4 with a first transverse web 6 and a second transverse web 8. In addition, in this exemplary embodiment there is a third transverse web 10, which is located between the first transverse web 6 and the second transverse web 8. The transverse webs 6, 8 and 10 are arranged in two mutually opposite lateral holders 12 and are designed to stretch a fabric 14. The fabric 14 is substantially impermeable to gas and, together with the transverse webs 6, 8 and 10, forms the actual mask adapted to the person's face.

At least the first transverse web 6 is flexible. In the exemplary embodiment shown, the two other transverse webs 8 and 10 are also flexible and allow relatively free shaping. The transverse webs 6, 8 and 10 are mounted displaceably in the holders 12. For this purpose, the lateral holders 12 have for each transverse web 6, 8 and a rectilinear cavity 16 into which the relevant transverse web 6, 8 and 10 is inserted. By pulling the lateral holders 12 outward and apart, the transverse webs 6 slide partially out from the cavities 16, such that the width of the oxygen mask 2 is thereby increased, if necessary.

In the fabric 14 there is an exhalation valve 18, which is provided to lead used air out of the mask. An oxygen supply line 20 extends from an oxygen source (not shown here) through the fabric 14 and, on an inside 22 (concealed in the plane of the drawing) directed toward the person, generates an oxygen-enriched atmosphere.

Furthermore, the oxygen mask 2 has a headband 24, which is mounted on the lateral holders 12 and is able to secure the oxygen mask 2 to a person's head. As is shown at schematically indicated attachment points 26 in the form of elongate recesses, the headband 24 is also able to be pulled out slightly from the lateral holders 12 in order to increase its effective length.

Figure 2:
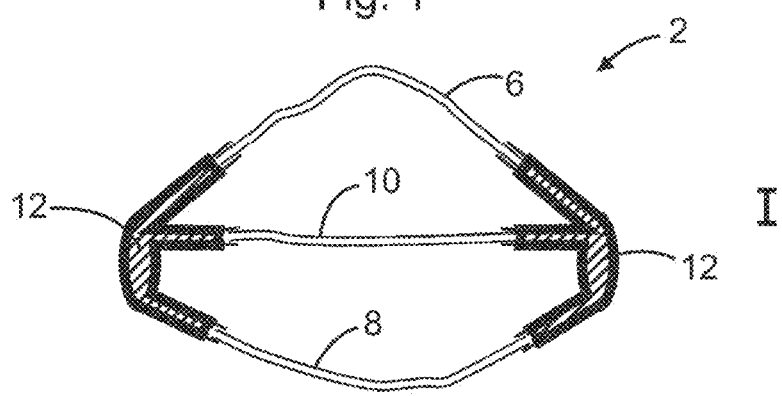
FIG. 2 shows different states of the transverse webs in three successive schematic illustrations.
Figure 2:
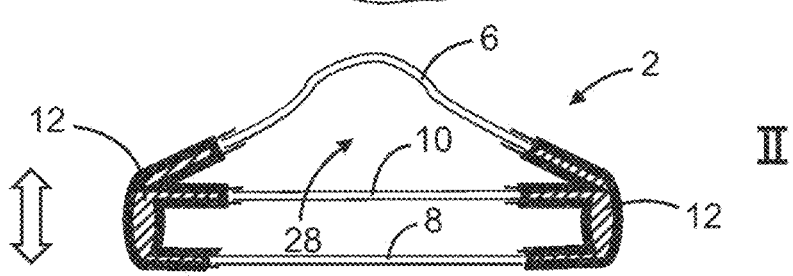
Figure 2:
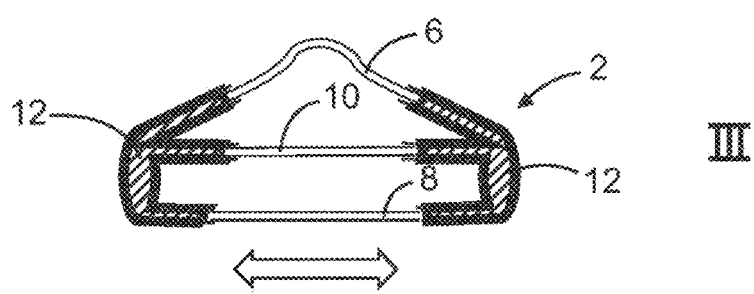

FIG. 2 shows the oxygen mask 2 in different states in three illustrations I, II and III. In illustration I, the oxygen mask 2 corresponds substantially to the illustration from FIG. 1. The transverse webs 6, 8 and 10 are at relatively large distances from each other, and therefore a fairly large face can be assumed. In II, the distances between the transverse webs 6, 8 and 10 are small. The flexibility of the transverse webs 6, 8 and 10 permits very easy deformation, such that, among other things, the distance between the transverse webs is variable. It is shown here, by way of example, that the first transverse web 6 has a region 28 which is preformed for adaptation to a person's nose or which has a preformed curvature. In III, a short distance between the lateral holders is shown, and at the same time a short distance between the transverse webs 6, 8 and 10. In this state, the oxygen mask 2 could be suitable in particular for the care of babies or infants.

Figure 3:
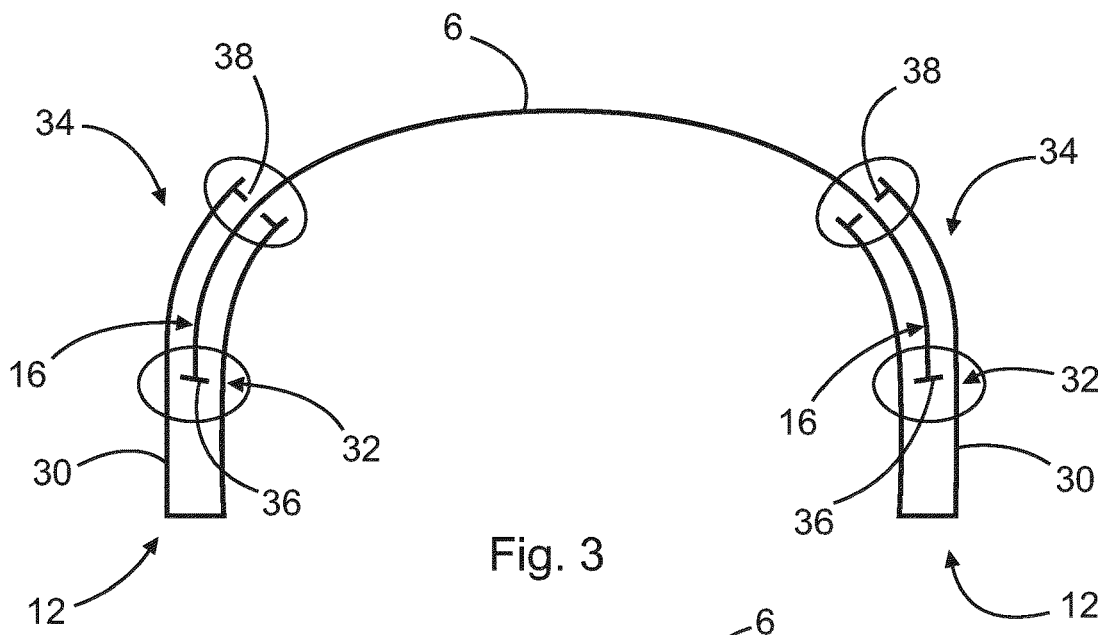
FIG. 3 shows a schematic detailed section through lateral holders and a transverse web.

FIG. 3 shows a detail of a lateral holder 12 and of the first transverse web 6. The designs can also be applied to the other transverse webs 8 and 10. By way of example, the lateral holder 12 has a plurality of holding portions 30, in each of which the aforementioned cavity 16 is formed. An end 32 of the first transverse web 6 runs in the cavity 30 and is able to adopt a variable insertion depth. To prevent the end 32 from being pulled completely out of the cavity 16, a limiting device 34 is provided. The latter is in the form of an end-side thickening 36 on the first transverse web 6 and an end-side tapering 38 on the cavity 16. If the first transverse web 6 is pulled out from the cavity 30, the end-side thickening 36 and the end-side tapering 38 of the cavity 16 come into surface contact and prevent further movement. This is provided on both sides of the first transverse web 6, i.e. on both lateral holders 12 or on holding portions 30 arranged thereon.

Figure 4:
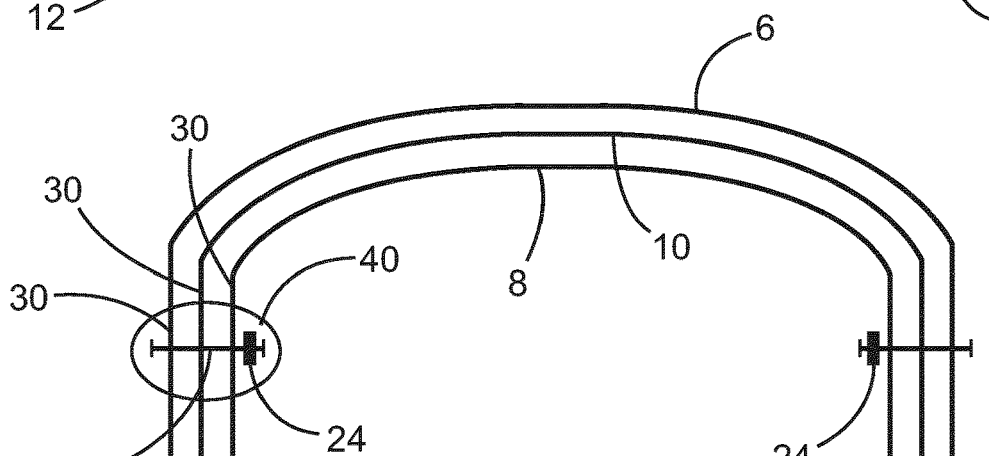
FIG. 4 shows a schematic illustration of transverse webs held in a hinged manner.

FIG. 4 shows the three transverse webs 6, 8 and 10, each arranged in a respective holding portion 30. The three holding portions 30 are connected to one another by a hinge 40 which, in the case shown, has a pin-like component 42 and extends all the way through the three holding portions 30. The holding portions 30 can then be fanned out to different extents and thus increase or decrease the surface area spanned by the transverse webs 6, 8 and 10. The headband 24 could also be secured at the hinge 40.

Figure 5:
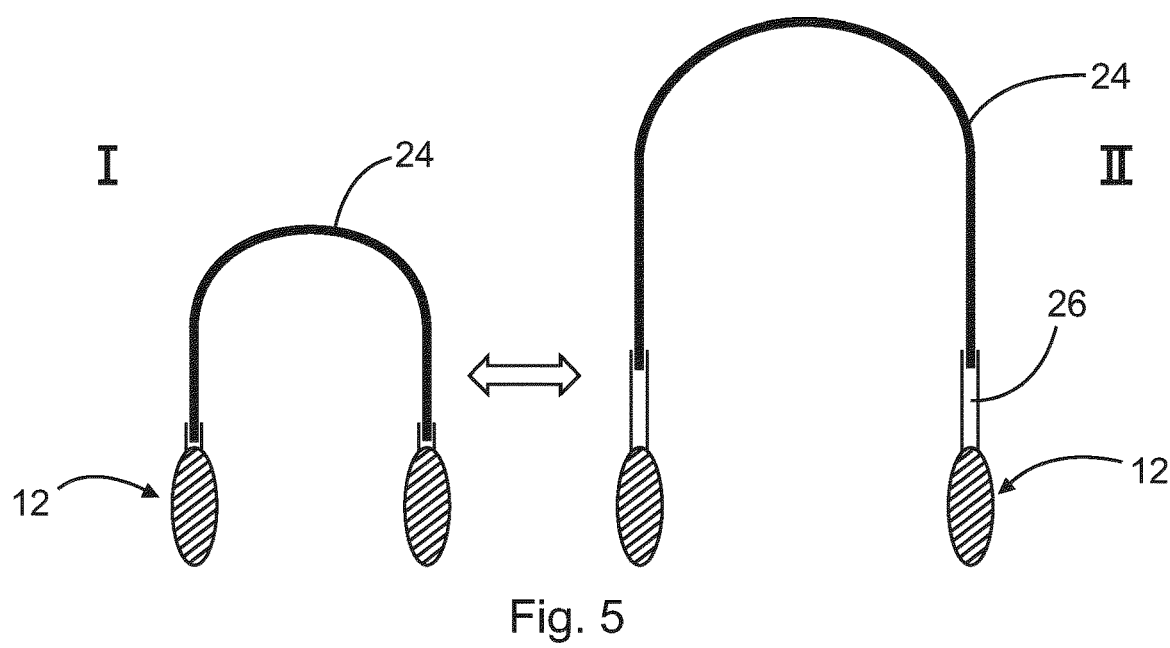
FIG. 5 shows two views of the headband in two different positions.

FIG. 5 shows the headband 24 in two different illustrations I and II. In I, the headband 24 is shortened by being pushed into the lateral holders 12 or the attachment points 26, whereas in II the headband 24 is pulled out. This therefore permits an adaptation to different head sizes.

Figure 6:
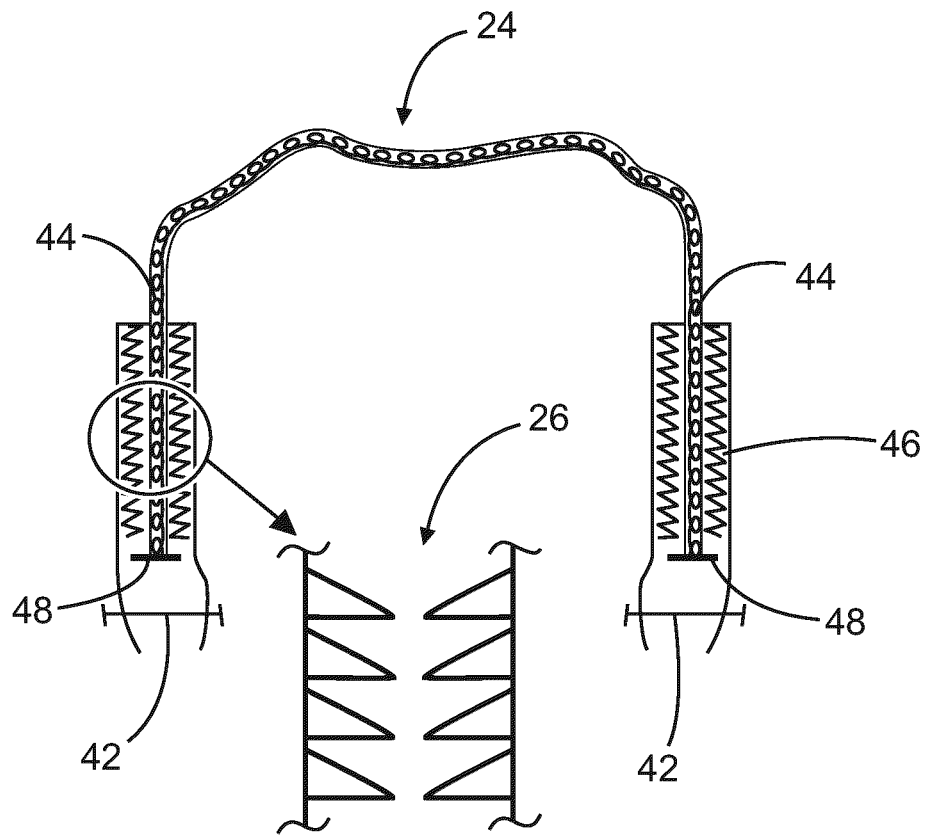
FIG. 6 shows a schematic detailed section through the attachment of the headband to the lateral holders.

FIG. 6 shows, by way of example, that the headband 24 has a stiffened end portion 44 that engages in the attachment point 26. In the cavity present there, sawtooth-like projections 46, for example, are provided which act radially on the stiffened portions 44. This generates a certain mechanical resistance. It is also conceivable here that an incremental displacement is obtained in which the stiffened portions 44 are provided with grooves that are able to come into engagement with the projections 46. To prevent the stiffened portions 44 from being pulled out completely, end stops 48 are provided. These can come into surface contact with the innermost projections 46 in order thereby to limit the pulling out.

Figure 7:
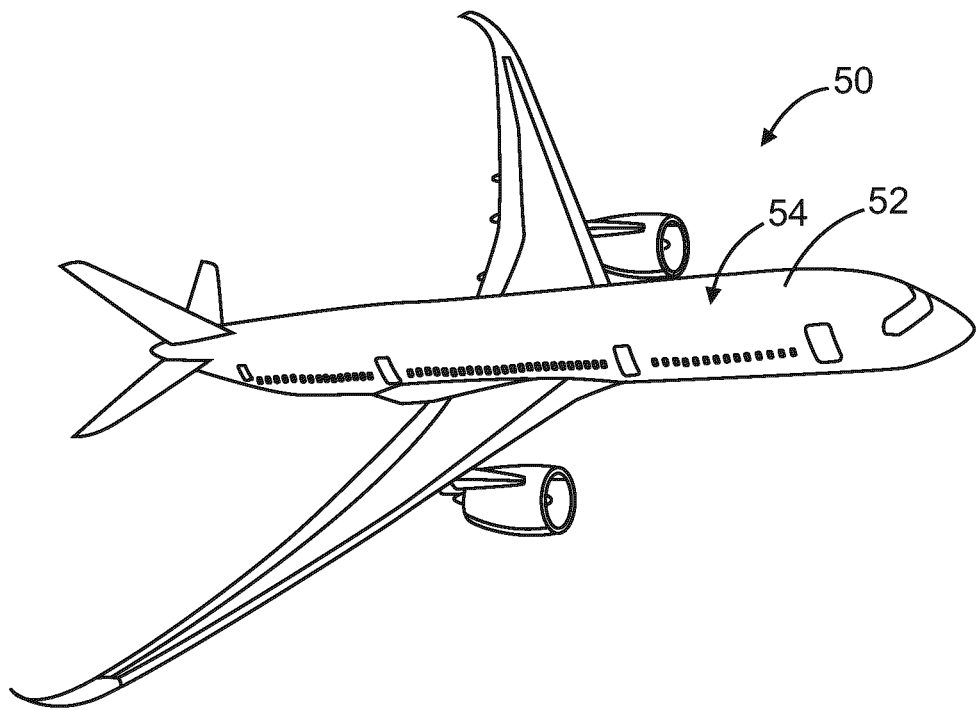
FIG. 7 shows an aircraft in which oxygen masks are provided.

FIG. 7, finally, shows a passenger aircraft 50 that has a fuselage 52 with a cabin 54 formed therein. A plurality of oxygen masks 2 can be arranged there.

It will additionally be noted that "having" is not exclusive of other elements or steps, and "a" or "an" is not exclusive of a multiplicity. Furthermore, it will be noted that features that have been described with reference to one of the exemplary embodiments above can also be used in combination with other features of other exemplary embodiments described above. Reference signs in the claims should not be regarded as a limitation.

REFERENCE SIGNS 2 oxygen mask
4 holding frame
6 first transverse web
8 second transverse web
10 third transverse web
12 lateral holder
14 fabric
16 cavity
18 exhalation valve
20 oxygen supply line
22 inside
24 headband
26 attachment point/recess
28 region with preformed curvature 30 holding portion
32 end
34 limiting device
36 thickening
38 tapering
40 hinge
42 pin-like component
44 stiffened end portion
46 projection
48 end stop
50 passenger aircraft/aircraft
52 fuselage
54 cabin

The invention claimed is:

1. An oxygen mask for supplying oxygen to a person, comprising:
   a holding frame having a plurality of transverse webs;
   a substantially gas-impermeable fabric arranged on the holding frame and stretchable by the plurality of transverse webs;
   a headband connected to the holding frame;
   an exhalation valve arranged on the fabric and passing through the fabric; and
   an oxygen supply line for providing oxygen to an inside of the oxygen mask,
   wherein the plurality of transverse webs is arranged in first and second lateral holders lying opposite each other,
   wherein the plurality of transverse webs is flexible,
   wherein the distance of the first and second lateral holders from each other is adjustable at least between a first and a second distance,
   wherein the first and second lateral holders have a plurality of holding portions, each of the plurality of holding portions configured for receiving one of the plurality of transverse webs, and
   wherein the plurality of transverse webs is mounted displaceably on or in the first and second lateral holders, the plurality of transverse webs displaceable relative to the corresponding holding portions.

2. The oxygen mask as claimed in claim 1, wherein at least one of the first and second lateral holders has a rectilinear cavity adapted to the relevant one of the plurality of transverse webs, such that the relevant one of the plurality of transverse webs is configured to be pushed into the rectilinear cavity to different depths.

3. The oxygen mask as claimed in claim 2, wherein the rectilinear cavity and the relevant one of the plurality of transverse webs have a limiting device configured to prevent the relevant one of the plurality transverse webs from being pulled out completely.

4. The oxygen mask as claimed in claim 3, wherein the limiting device is in the form of an end-side thickening of the relevant one of the plurality of transverse webs and an end-side tapering of the rectilinear cavity.

5. The oxygen mask as claimed in claim 1, wherein the fabric is stretchable between a first of the plurality of transverse webs and a second of the plurality of transverse webs.

6. The oxygen mask as claimed in claim 5, wherein the plurality of transverse webs comprises a third transverse web arranged between the first transverse web and the second transverse web.

7. The oxygen mask as claimed in claim 5, wherein the holding portions are arranged on a hinge configured to fan the holding portions out variably in relation to one another for adaptation to a person.

8. The oxygen mask as claimed in claim 1, wherein the first and second lateral holders are formed from an elastic material.

9. The oxygen mask as claimed in claim 1, wherein one of the plurality of transverse webs has a preformed curvature in parts, is the preformed curvature shaped to nestle on a nose of a person.

10. The oxygen mask as claimed in claim 1, wherein the first and second lateral holders and the plurality of transverse webs are made of silicone, a silicone-like material, an elastomer or a rubber-like material.

11. The oxygen mask as claimed in claim 1, wherein the headband has two stiff end portions which each engage in a toothed recess, wherein the headband and the toothed recesses are configured to change an effective length of the headband in increments.

12. The oxygen mask as claimed in claim 1, wherein the oxygen supply line protrudes through the fabric to the inside of the oxygen mask.

13. A system for providing oxygen to oxygen masks in an aircraft, comprising:
   an oxygen source; and
   one or more oxygen masks as claimed in claim 1,
   wherein the oxygen supply line of the oxygen masks are each connectable to the oxygen source.

14. An aircraft comprising a passenger cabin and at least one system as claimed in claim 13.

* * * * *